(12) United States Patent
Arsenault et al.

(10) Patent No.: US 6,577,143 B2
(45) Date of Patent: Jun. 10, 2003

(54) APPARATUS AND METHOD FOR DETERMINING A DRYING TIME OF A PIECE OF WOOD

(75) Inventors: François Arsenault, Saint-Siméon (CA); Paul Giasson, deceased, late of Bonaventure (CA); by Héléne Giasson, executrix, Victoriaville (CA); Gilles Arsenault, Saint-Simeon (CA)

(73) Assignee: Fabrication Delta, Inc., Saint-Simeon (CA)

( * ) Notice: Subject to any disclaimer, the term of this patent is extended or adjusted under 35 U.S.C. 154(b) by 0 days.

(21) Appl. No.: 09/982,186

(22) Filed: Oct. 18, 2001

(65) Prior Publication Data

US 2002/0067173 A1 Jun. 6, 2002

(30) Foreign Application Priority Data

Oct. 18, 2000 (CA) ............................................. 2323859

(51) Int. Cl.⁷ ............................................. G01R 27/04
(52) U.S. Cl. .......................... 324/689; 324/694; 73/73
(58) Field of Search ................................ 324/632, 639, 324/640, 643, 664, 687, 689, 691, 694; 73/579, 597, 73, 866

(56) References Cited

U.S. PATENT DOCUMENTS 3,811,087 A      5/1974   Schmelzer ............. 324/58.5 A
4,059,988 A     11/1977   Shaw ........................... 73/579
4,123,702 A     10/1978   Kinanen et al. ........ 324/58.5 A
4,377,783 A      3/1983   Wagner .................... 324/61 R
4,683,418 A      7/1987   Wagner et al. ............. 324/61 P
4,876,889 A     10/1989   Shakkottai et al. ........ 73/336.5
5,307,679 A      5/1994   Ross ........................... 73/597
5,317,274 A      5/1994   Nakagawa et al. ......... 324/678
5,406,378 A      4/1995   Jamroz et al. .............. 356/445
5,486,815 A      1/1996   Wagner ...................... 340/602

FOREIGN PATENT DOCUMENTS

CA          1326908         2/1994
CA          2270274        11/1999

*Primary Examiner*—N. Le
*Assistant Examiner*—Vincent Q. Nguyen
(74) *Attorney, Agent, or Firm*—Collard & Roe, P.C.

(57) ABSTRACT

The drying time of a piece of wood can be determined by the present apparatus and method, based on a current signal passing through the piece of wood. A set of first and second electrodes of a probe are inserted into the piece of wood which may be travelling on a conveyor. The second electrode has an input for receiving electric power. The first electrode has an output for transmission of the current signal having passed through the piece of wood. The probe is driven toward and away from the piece of wood by a driving mechanism controlled by a control circuit. A measuring circuit is coupled to the outputs of the electrodes. The current signals are measured by the measuring circuit, which determines the drying time of the piece of wood.

22 Claims, 9 Drawing Sheets

FIG. 12 though their initial humidity levels are identical.

APPARATUS AND METHOD FOR DETERMINING A DRYING TIME OF A PIECE OF WOOD

FIELD OF THE INVENTION

The present invention relates to an apparatus and a method for determining the drying time of a piece of wood among wood species, such as fir and spruce.

BACKGROUND OF THE INVENTION

It is standard practice in the lumber industry to dry or season several lumber pieces together for a certain period of time before these can be used or sold to customers. In a typical sawmill, once the wood has been cut to a specific length, the lumber pieces are put in a dryer. However, since not all lumber pieces have the same humidity level, some may be over-dried while others may remain too humid. Consequently, the quality of the lumber pieces becomes inferior as they are prone to twist, split or rot. One solution to this problem has been to sort or classify the lumber pieces according to their humidity level before the drying operation. An hygrometer is used to determine the humidity of each piece of wood. However, such classification does not yield satisfactory results because the measurement of humidity before the drying operation is not necessarily correlated with its drying time. For example, pieces of wood of different species may require different drying times even As seen above, there is a need to determine the drying time of a piece of wood in a simple and effective manner, which would lead to a more efficient sorting of the lumber pieces before the drying step.

Known in the art, Canadian Patent No. 1,326,908 (BEAUCHEMIN et al.) provides a method and an apparatus for detecting the humidity in cut lumber before sorting and drying the same. However, the apparatus uses weight sensors that are inadequate for precisely measuring the humidity level in the lumber pieces. Indeed, tests have shown that the weight of a piece of wood is not necessarily related to its humidity level. Furthermore, as mentioned above the determination of the humidity level in a piece of wood is not necessarily an indication of its drying time.

Also known in the art, Canadian Patent Application 2,270,274 (LEGER et al.) describes a method and an apparatus for facilitating the separation of lumber pieces that are of different species. The lumber pieces are coated with an indicator liquid and are optically scanned to identify their species prior to drying. The process is inefficient as it does not determine the drying time of a piece of wood and additionally requires the marking of each piece at an earlier step.

Also known in the art are U.S. Pat. Nos. 5,486,815 (WAGNER); 5,406,378 (JAMROZ et al.); 5,307,679 (ROSS); 5,317,274 (NAKAGAWA et al.); 4,876,889 (SHAKKOTTAI et al.); 4,683,418 (WAGNER et al.); 4,377,783 (WAGNER); 4,123,702 (KINANEN et al.); 4,059,988 (SHAW); 3,811,087 (SCHMELZER), which show various devices for measuring humidity of different materials or determining a species of a piece of wood, but are all unable to determine the drying time of a piece of wood in a simple and effective manner.

SUMMARY OF THE INVENTION

An object of the present invention is to provide a simpler and more effective apparatus and method for determining the drying time of a piece of wood and which does not suffer from the drawbacks of the prior art.

Another object of the invention is to provide a method and an apparatus for determining the drying time of a lumber piece, which is reliable and adapted to large scale sawmills, and can be used in a fully automated implementation.

According to the present invention, there is provided an apparatus for determining a drying time of a piece of wood, comprising:

a conveyor adapted to transport the piece of wood along a travelling path;

a probe mounted aside the travelling path, the probe having first and second electrodes extending next to one another and having spiked ends directed toward the travelling path for insertion into the piece of wood when the piece of wood transported by the conveyor passes by the probe, the second electrode having an input for receiving electric power, the first electrode having an output for transmission of a current signal having passed through the piece of wood from the second electrode to the first electrode;

driving means for selectively driving the probe toward and away from the piece of wood between a measuring position where the spiked ends of the electrodes are stuck in the piece of wood and a retracted position where the spiked ends of the electrodes are withdrawn from the piece of wood;

a control means connected to the driving means, for controlling operation thereof; and a measuring means coupled to the outputs of the electrodes, for measuring the current signal, and determining the drying time of the piece of wood based on the current signal.

According to another aspect of the present invention, there is provided a method for determining a drying time of a piece of wood, using a probe having first and second electrodes extending next to one another and having spiked ends in a same direction, comprising the steps of:

transporting the piece of wood along a travelling path;

driving the probe against the piece of wood into a measuring position where the spiked ends of the electrodes are stuck in the piece of wood;

applying electric power on the second electrode while the spiked ends of the electrodes are in the measuring position;

measuring a current signal passing through the piece of wood from the second electrode to the first electrode;

removing the probe from the piece of wood into a retracted position where the spiked ends of the electrodes are withdrawn from the piece of wood when the current signal has been measured; and determining the drying time of the piece of wood based on the current signal.

According to yet another aspect of the present invention, there is provided an apparatus for determining a drying time of a piece of wood, comprising:

a probe having first and second electrodes extending next to one another and having spiked ends directed in a same direction for insertion into the piece of wood, the second electrode having an input for receiving electric power, the first electrode having an output for transmission of a current signal having passed through the piece of wood from the second electrode to the first electrode; and a measuring means coupled to the output of the first electrode, for measuring the current signal, and determining the drying time of the piece of wood based on the current signal.

According to still another aspect of the present invention, there is provided a method for determining a drying time of a piece of wood, using a probe having first and second electrodes extending next to one another and having spiked ends in a same direction, comprising the steps of:

driving the probe against the piece of wood into a measuring position where the spiked ends of the electrodes are stuck in the piece of wood;

applying electric power on the second electrode while the spiked ends of the electrodes are in the measuring position;

measuring a current signal passing through the piece of wood from the second electrode to the first electrode;

removing the probe from the piece of wood when the current signal has been measured; and determining the drying time of the piece of wood based on the current signal.

The invention as well as its numerous advantages will be better understood by reading of the following non restrictive description of preferred embodiments made in reference to the appended drawings.

DESCRIPTION OF PREFERRED EMBODIMENTS

Figure 2:
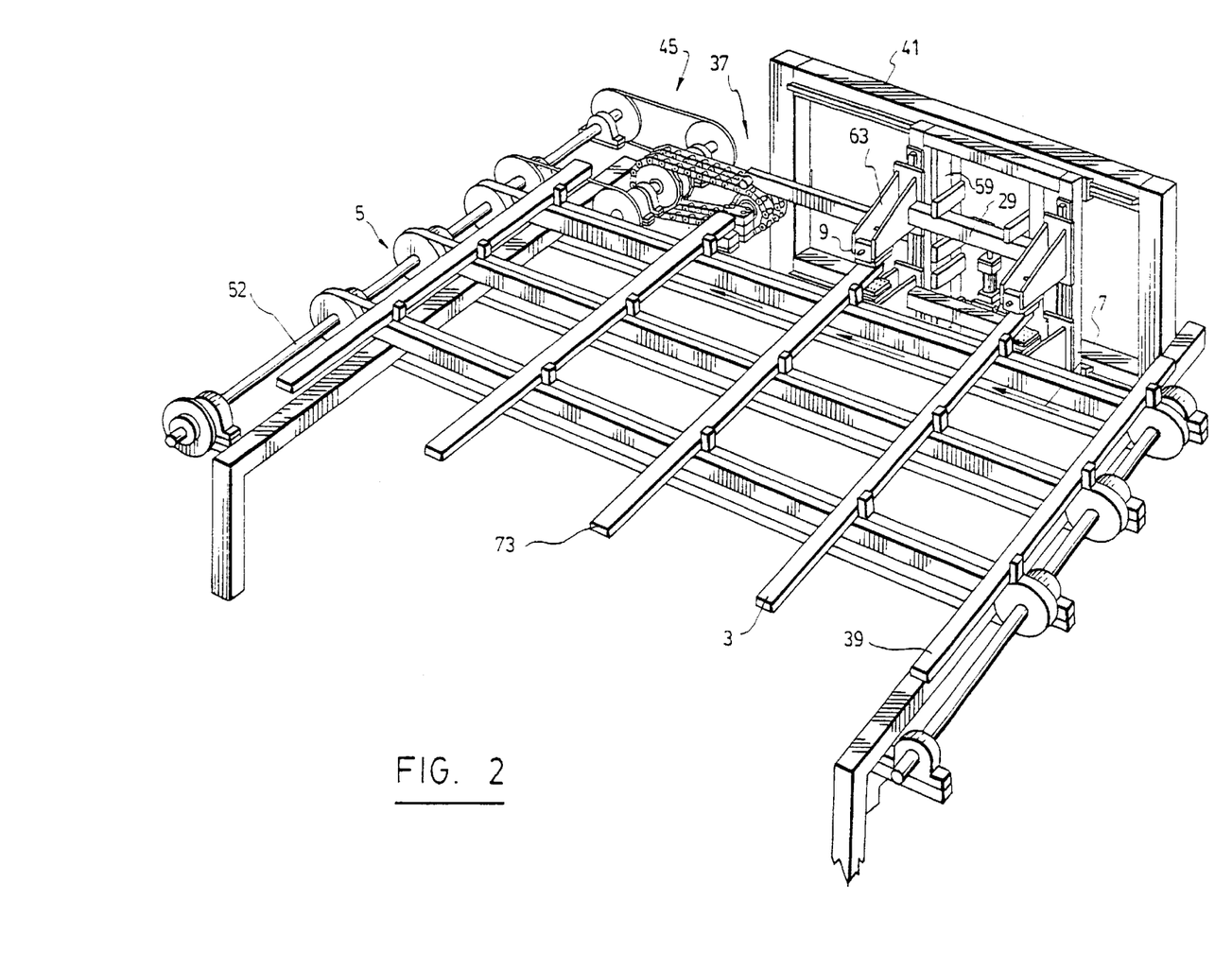
FIG. 2 is a perspective view of an apparatus for transporting pieces of wood and determining their drying time, according to the present invention.

Referring to FIG. 2, there is shown an apparatus for determining the drying time of a piece of wood 3, such as fir and spruce or other species, according to the present invention. The apparatus comprises a conveyor 5 adapted to transport the piece of wood 3 along a travelling path in the direction depicted by arrow 7. The conveyor 5 may be a conventional conveyor used in sawmills for transporting pieces of wood after these have been cut to a specific length.

Figure 9:
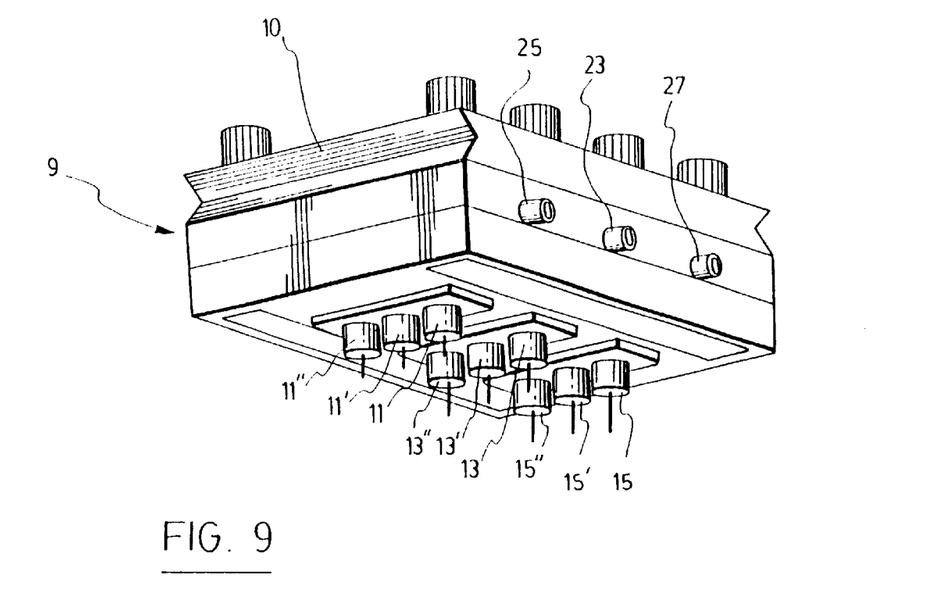
FIGS. 9, 10 and 11 are a perspective view, a side view and a top view respectively of a probe according to the present invention.
Figure 10:
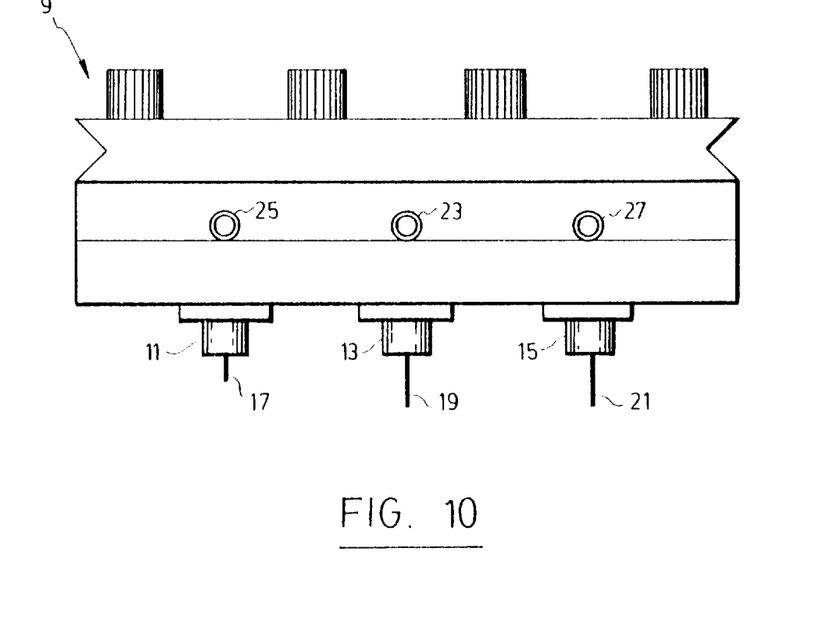
Figure 11:
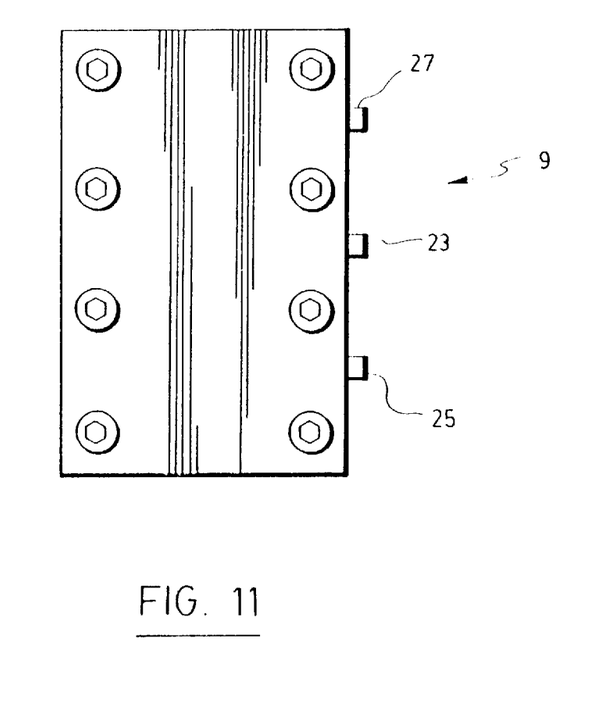

The apparatus also comprises a probe 9 mounted aside the travelling path 7 along which path the piece of wood 3 is transported. As best seen in FIGS. 9 to 11, the probe 9 has first and second electrodes 11, 13 and an optional third electrode 15 extending next to one another and having spiked ends 17, 19, 21 directed toward the travelling path for insertion into the piece of wood 3 transported by the conveyor 5 when it passes by the probe 9. The second electrode 13 has an input 23 for receiving electric power. The first and third electrodes 11, 15 are spaced from the second electrode 13 in opposite directions and have outputs 25, 27 for transmission of current signals having passed through the piece of wood 3 from the second electrode 13 to the first and third electrodes 11, 15 respectively. The first and third electrodes 11, 15 may have different dimensions. The third electrode 15 is optional as it is provided for redundancy purposes and to determine the homogeneity of the piece of wood as will be described below.

For example, in use, if one of the spiked ends 17, 21 of the first and third electrodes 11, 15 is inadvertently inserted into a knot in the piece of wood 3, then this would probably yield an erroneous measurement which would not be close to the one measured by the other electrode. This extraneous measurement could then be discarded by an appropriate filter or in a software program that analyses the results.

Also, by using the three electrodes 11, 13, 15, experimental tests performed by the applicant have demonstrated that in addition of determining the drying time, one can determine the homogeneity of the piece of wood 3. Indeed, if the piece of wood 3 is homogeneous, then the measured current signals are substantially identical for each of the first and third electrodes 11, 15, whereas if the piece of wood 3 is heterogeneous, then the measured current signal are different for each of the first and third electrodes 11, 15.

Preferably, the spiked end 17 of the first electrode 11 is shorter than the spiked end 21 of the third electrode 15. The spiked end 17 of the first electrode is, in this example, 3/16 inches (0.476 cm) long, whereas the spiked ends 19, 21 of the second and third electrodes 13, 15 measures 7/16 inches (1.111 cm) long. However, all the spiked ends 17, 19, 21 may be of the same length. Also, it is preferable that the electrodes 11, 13, 15 be aligned with and equally spaced apart from one another.

Preferably, the electrodes 11, 13, 15 are made of special steel which is highly wear resistant and sufficiently rigid. The electrodes 11, 13, 15 can be mounted on an electrode assembly 10 designed for easy replacement of any electrode.

Referring back to FIG. 2, the apparatus also comprises a driving mechanism 29 for selectively driving the probe 9 toward and away from the piece of wood 3 between a measuring position where the spiked ends 17, 19, 21 of the electrodes 11, 13, 15 are stuck in the piece of wood 3, and a retracted position where the spiked ends 17, 19, 21 of the electrodes 11, 13, 15 are withdrawn from the piece of wood 3.

Figure 1:
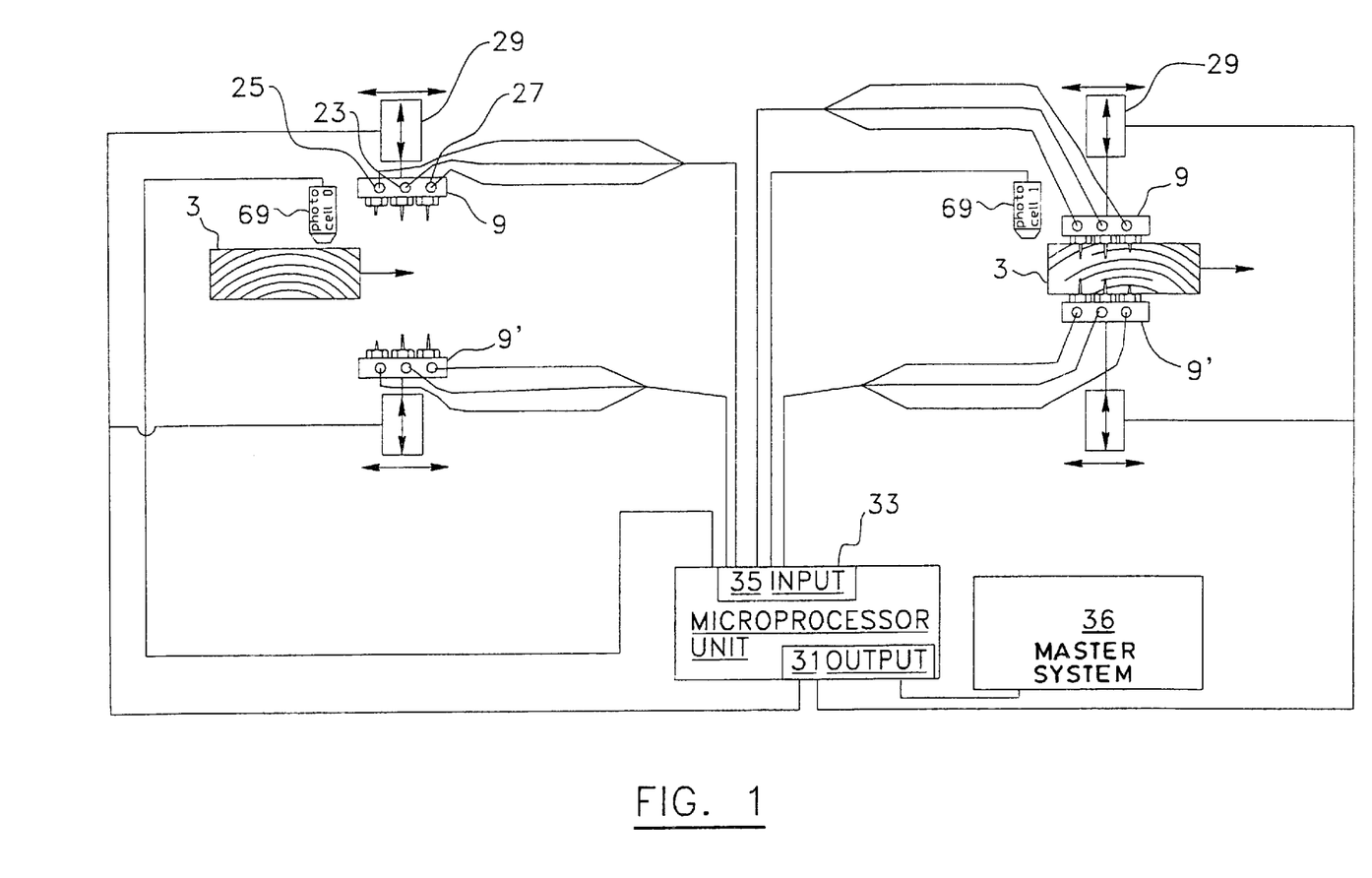
FIG. 1 is a schematic block diagram of an apparatus for determining a drying time of a piece of wood, according to the present invention.

Referring to FIG. 1, the apparatus also comprises a control circuit 31 connected to the driving mechanism 29, for controlling its operation. The control circuit 31 can be conveniently embodied by a control module in a microprocessor unit 33. A measuring circuit 35 coupled to the outputs 25, 27 of the electrodes 11, 15 is provided for measuring the current signals having passed through the piece of wood 3. The measuring circuit 35, which can be conveniently embodied by a measuring module in the microprocessor unit 33, determines the drying time of the piece of wood 3 based on the current signals.

The measuring circuit 35 that was used in the experiments is a microcomputer made by the company MOELLER. It receives the current signals and has an analog to digital converter and microprocessor for computing digital values corresponding to the measured current signals. The microcomputer can be programmed to convert these digital values into resistance values. The exact resistance that corresponds to each digital value is determined by measuring the digital values of different nominal resistances with the electrodes 11, 13, 15. The results are then tabulated and can be integrated in the programming of the microcomputer or measuring circuit 35 that was mentioned above.

In operation, the apparatus of the present invention can provide a drying time for each piece of wood that is probed by the electrodes as the measured current signals are processed by the microcomputer or measuring circuit 35. This drying time may be displayed by the microcomputer or can be transmitted to another machine that sorts the pieces of wood according to the drying time data.

The measuring circuit 35 can also determine the homogeneity level of the piece of wood 3 based on a difference between the current signals. If a significant difference between the electrodes is detected by the measuring circuit, then the piece of wood is determined to be less homogeneous.

In the embodiment described above, only one probe 9 is needed to take the current signal measurements. However, if the piece of wood 3 is travelling on the conveyor 5 and if the apparatus is not provided with a mechanism for moving the probe along the conveyor, it may be necessary to stop or slow down the conveyor 5 so that the spiked ends 17, 19, 21 of the probe 9 can be inserted and removed from the piece of wood 3 without damaging the probe 9. The probe 9 is preferably made of a strong material providing high electric insulation resistance between the electrodes 11, 13, 15 and the electrode assembly 10. The microprocessor unit 33 may be also connected to a master system 36 that controls other mechanisms or parts in the sawmill.

Preferably, and as best shown in FIG. 9, the probe 9 comprises at least one set of first, second and third additional electrodes 11', 11", 13', 13", 15', 15" projecting on sides of and being connected with the first, second and third electrodes 11, 13, 15 respectively. The additional electrodes 11', 11", 13', 13", 15', 15" have substantially identical shapes to the electrodes connected therewith. These additional electrodes are useful for improving the reliability of the current measurements in the event that some of the electrodes run into knots in the wood, holes, or rotten parts, which would lead to erroneous measurements.

Figure 3:
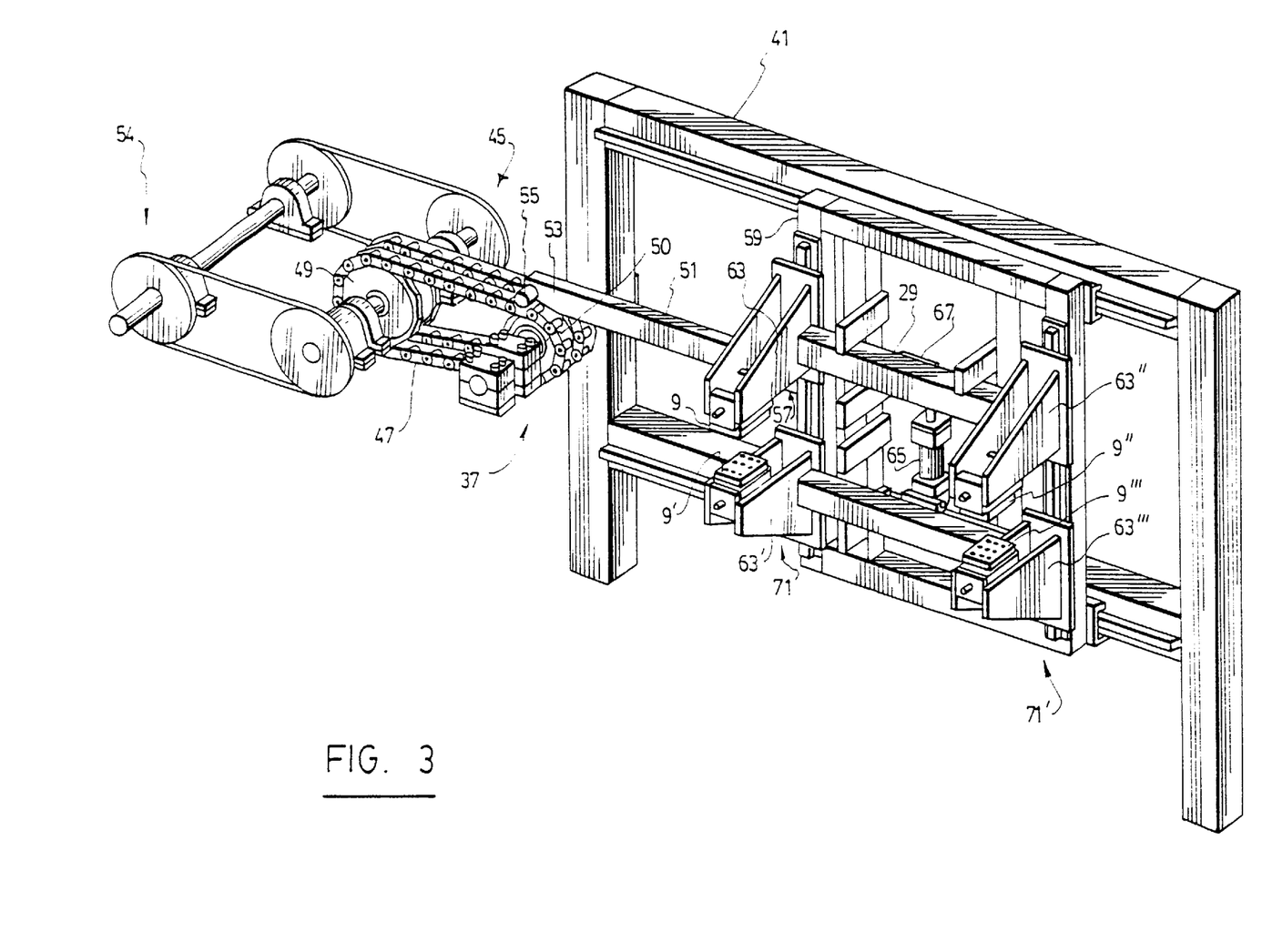
FIG. 3 is a perspective view of mechanisms for moving probes vertically and longitudinally according to the present invention.

Referring to FIGS. 2 and 3, the apparatus preferably includes a probe moving mechanism 37 mounted on a side of the conveyor 5. As will it be further described herein below, at least a portion of the probe moving mechanism 37 supports the driving mechanism 29. The probe moving mechanism 37 moves the probe 9 upstream along the conveyor 5 towards a subsequent piece of wood 39 travelling on the travelling path once the current signals passing through the piece of wood 3 have been measured by the measuring circuit 35.

The probe moving mechanism 37 may consist of a guide frame 41 mounted on the side of the conveyor 5. The guide frame 41, which is best shown on FIG. 4, has an arrangement of two parallel slides 43 receiving and guiding the driving mechanism 29 along the conveyor 5. A chain assembly 45 has a chain element 47 running around two spaced apart sprocket wheels 49, 50 mounted on the side of the conveyor 5 at a given distance from the guide frame 41. The chain assembly 45 can be driven by the conveyor 5 by coupling the sprocket wheel 49 to a turning shaft 52 of the conveyor 5 through a gearing assembly 54. A rod 51 extends between the guide frame 41 and the chain assembly 45. The rod 51 has an end pivotally connected to a link 55 of the chain element 47 and an opposite end 57 pivotally connected to the driving mechanism 29.

Figure 4:
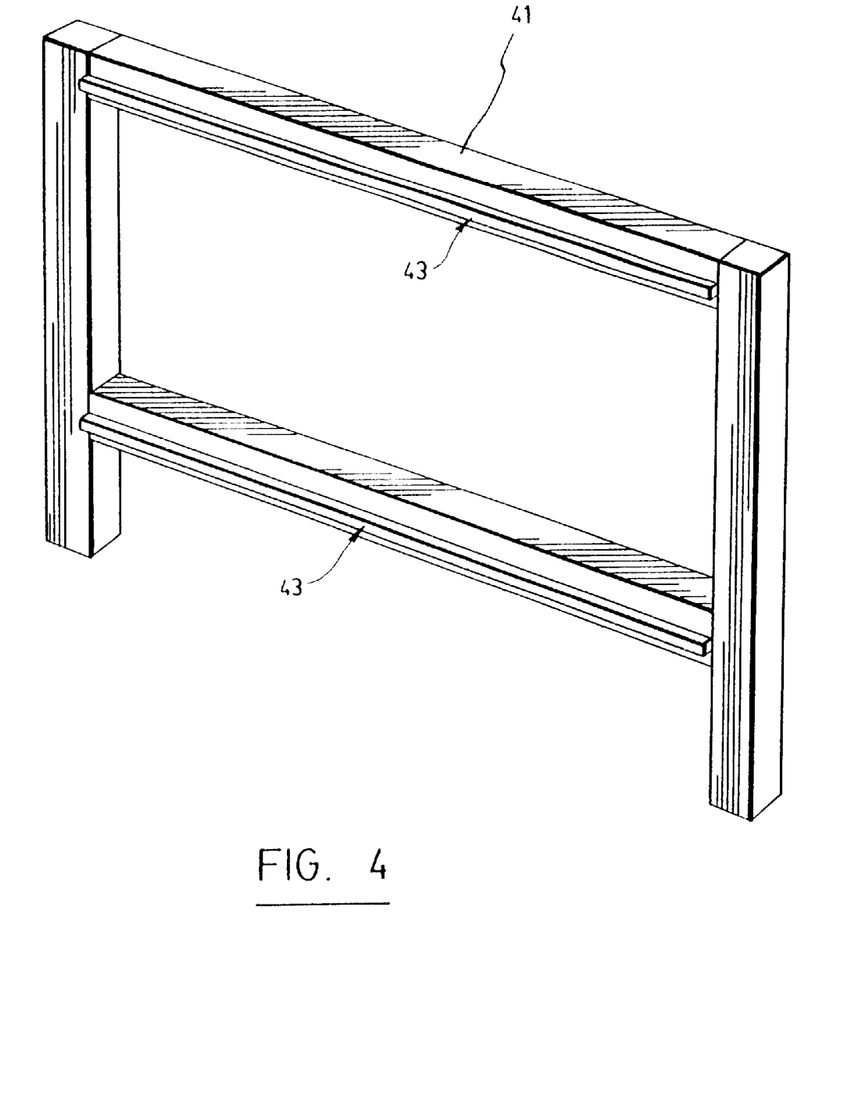
FIG. 4 is a perspective view of a guide frame for longitudinal motion of the probes, according to the present invention.

In operation, the probe moving mechanism 37 acts as a piston that moves the probe 9 back and forth linearly along the conveyor 5, and at the speed of the conveyor 5.

Figure 5:
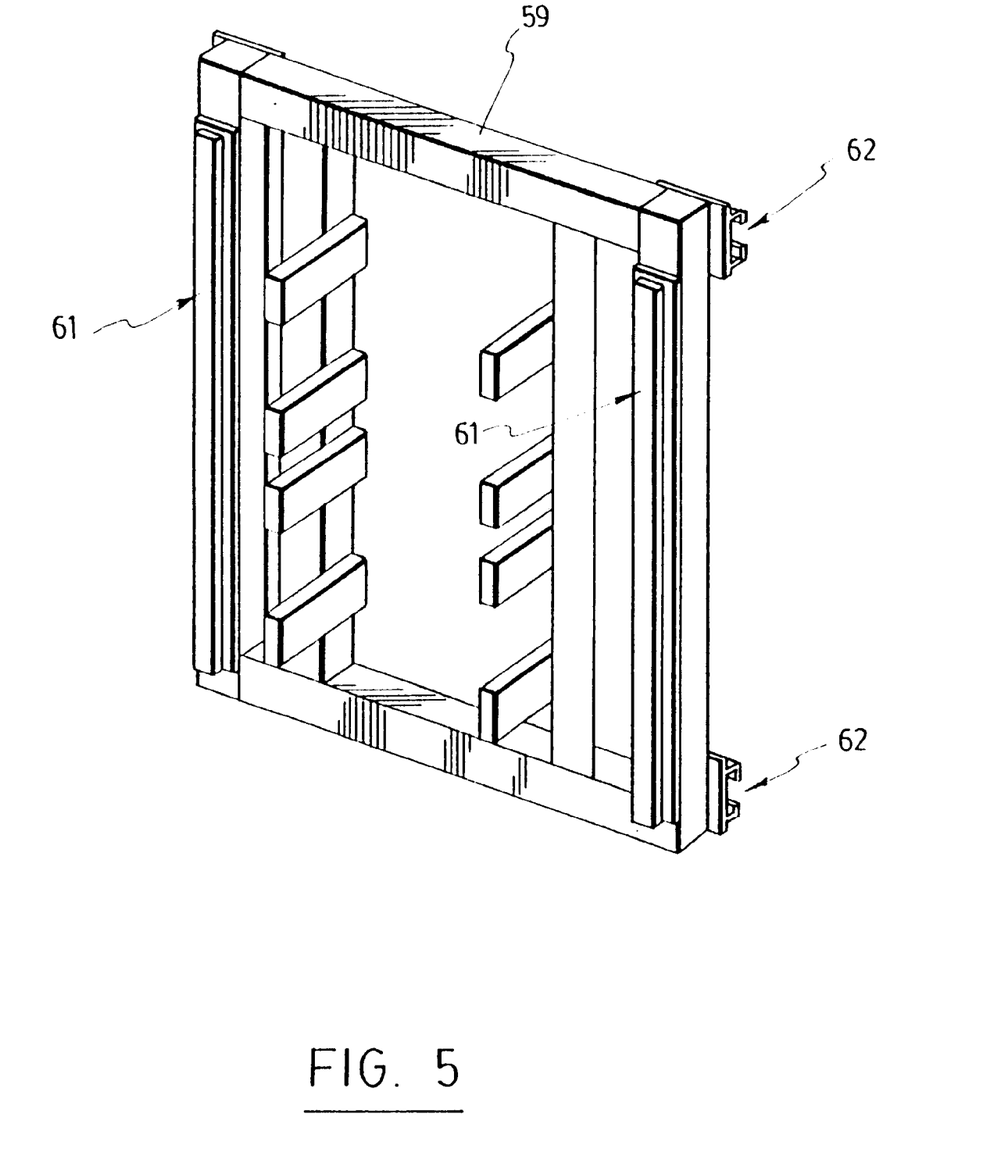
FIG. 5 is a perspective view of a base for vertical motion of the probes, according to the present invention.
Figure 6:
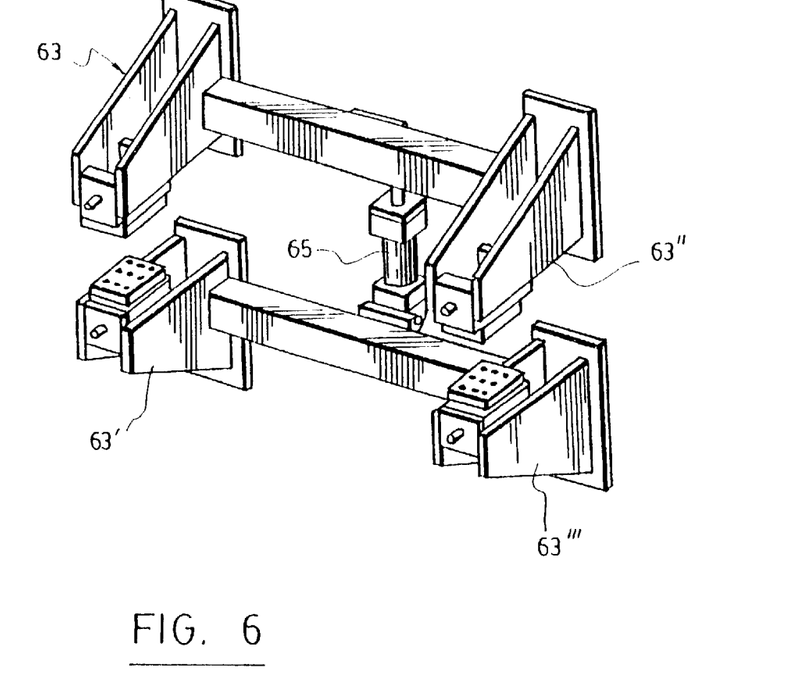
FIGS. 6, 7 and 8 are a perspective view, a side view and a top view respectively of jaw arrangements moving the probes relative to passing pieces of wood, according to the present invention.
Figure 7:
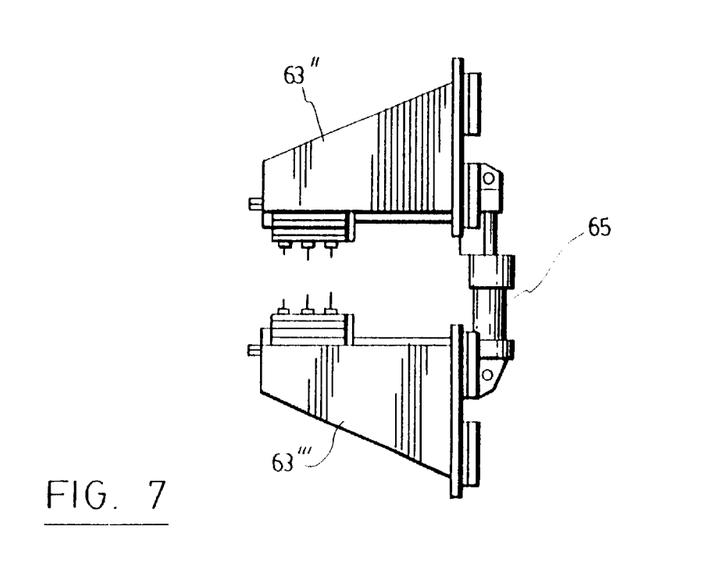

As best shown in FIG. 5, the driving mechanism 29 may be made of a base 59 slidably mounted in the arrangement of two parallel slides 43 of the guide frame 41. The back of the base 59 has a linear bearing engaging with the parallel slides 43 of the guide frame 41. The opposite end 57 of the rod 51 (see FIG. 3) can be pivotally attached to the base 59. The base 59 has an arrangement of two parallel slides 61 extending substantially crosswise to the arrangement of two parallel slides 43 of the guide frame 41.

Figure 8:
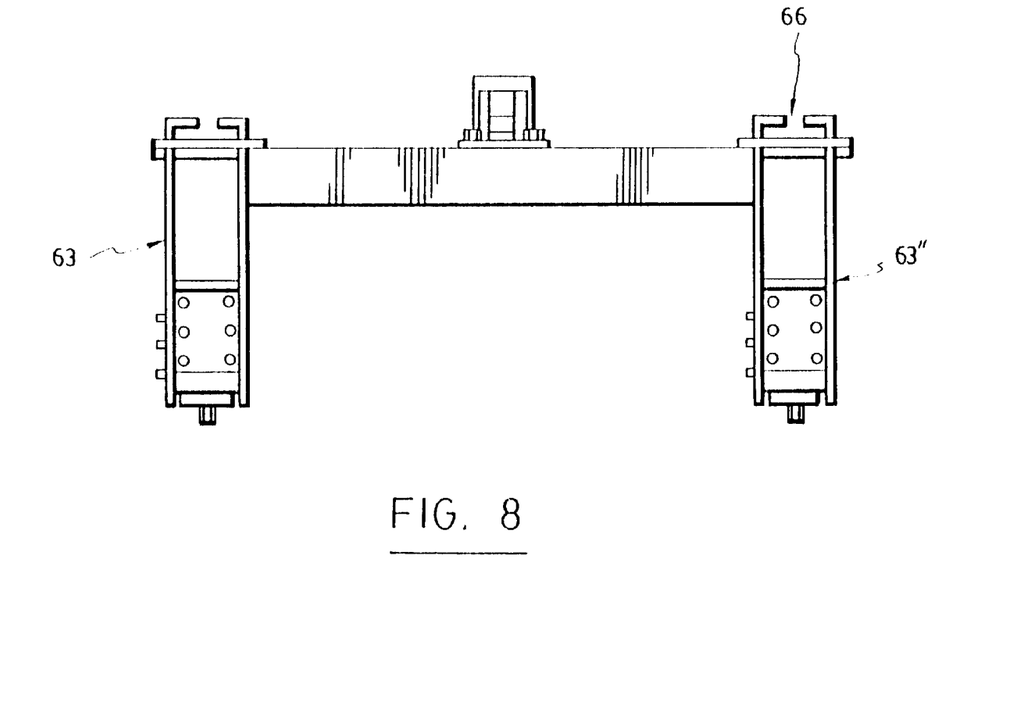

Referring back to FIGS. 2 and 3, a bracket 63 extends over the conveyor 5. The bracket 63 supports the probe 9 and forms part of the driving mechanism 29. The bracket 63 is slidably mounted in the arrangement of two parallel slides 61 of the base 59, and can slide toward and away from the conveyor 5. As best shown in FIG. 8, the back of the bracket 63 has a linear bearing 66 engaging with the parallel slides 61 of the base 59. An actuator 65 is further mounted onto the base 59 and has an end 67 connected to the bracket 63. The actuator 65 can push or pull the bracket 63 toward and away the conveyor 5 in response to control signals sent by the control circuit 31.

The actuator 65 may consist of a pneumatic piston with both a pressure regulator and a pneumatic electric valve. The actuator 65 may also consist of a hydraulic piston or other suitable actuating device.

Preferably, a detector 69 (see FIG. 1) is mounted in front of the probe 9 and is connected to the control circuit 31. The detector 69 generates a detection signal when the piece of wood 3 approaches the probe 9. The detector 69 may be formed of a photocell 69 directed across the travelling path 7 upstream of the probe 9.

An additional probe 9' can be mounted aside the travelling path, with both probes 9, 9' being identical and facing each other in a closable jaw arrangement 71 (see FIG. 3) for biting the piece of wood 3 by action of the driving mechanism 29.

In operation, when a current is sent to the actuator 65, the jaw arrangement 71 closes, whereas it opens when there is no current sent to the actuator 65.

An additional jaw arrangement 71' with facing probes 9", 9'" as in the other jaw arrangement 71 may be provided to process two pieces of wood at a time. Both jaw arrangements 71, 71' operate identically and in unison. The jaw arrangements 71, 71' are spaced from each other along the conveyor 5 so that the piece of wood 3 and a successive piece of wood 73 are processed simultaneously.

Because the pieces of wood travel on the conveyor at a relatively high speed, the measurements must be made quickly enough, e.g. about 150 pieces per minute. Therefore it is more efficient to use the above pair of jaw arrangements 71, 71' as two pieces of wood are bitten simultaneously. This configuration has the advantage of avoiding abrupt movements and undesirable vibrations.

Figure 12:
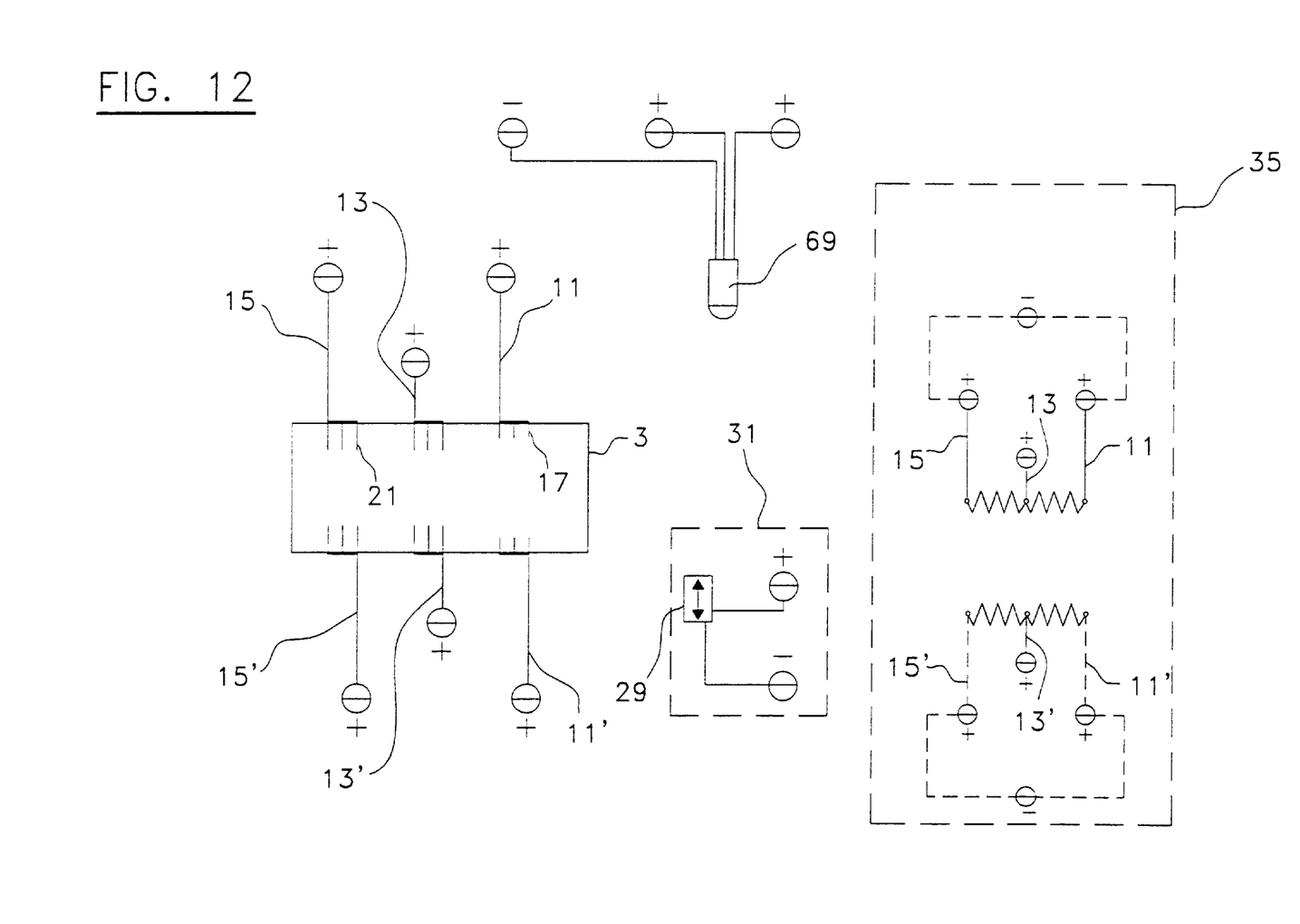
FIG. 12 is a schematic block diagram of control circuits of the apparatus, according to the present invention.

Referring to FIG. 12, there is shown a schematic circuit diagram of the electrodes 11, 11', 13, 13', 15, 15' being inserted in a piece of wood 3 as the second electrodes 13, 13' are powered with a 10 volts D.C. source. The spiked ends 17, 21 of the first and third electrodes 11, 15 measure $3/16$ inches (0.476 cm) and $7/16$ inches (1.111 cm) long respectively.

The drying time of a piece of wood is defined in the lumber industry as the time that it takes a piece of wood to attain a humidity level that is below 19%. As will be shown in the experimental results below, the drying time is correlated with the resistance measured by the measuring circuit.

In an experiment, the applicant has noted some measurements reported in the following table:

| Wood species | Resistance measured between the first and the second electrodes (kohms) | Resistance measured between the third and the second electrodes (kohms) | Approximate drying time (hours) |
| --- | --- | --- | --- |
| Fir | 375 | 375 | 220 |
| Fir | 200 | 200 | 262 |
| Fir | 150 | 150 | 340 |
| Fir | 40 | 40 | 400 |
| Fir | 10 | 10 | 800 |
| Spruce | 165 | 290 | 260 |
| Spruce | 75 | 130 | 240 |
| Spruce | 55 | 95 | 700 |

Further and more recent tests done by the applicant have been reported in the following tables:

| Wood species | Resistance measured between the first and the second electrodes (kohms) | Humidity level measured after 222 hours (%) |
| --- | --- | --- |
| Spruce | 120 | 16 |
| Spruce | 118 | 14 |
| Spruce | 84 | 15 |
| Spruce | 79 | 16 |
| Spruce | 79 | 15 |
| Spruce | 79 | 16 |
| Spruce | 74 | 15 |
| Spruce | 73 | 17 |
| Spruce | 72 | 18 |
| Spruce | 56 | 18 |
| Spruce | 44 | 19 |
| Spruce | 43 | 18 |
| Fir | 42 | 17 |
| Spruce | 42 | 18 |

| Wood species | Resistance measured between the first and the second electrodes (kohms) | Humidity level measured after 288 hours (%) |
| --- | --- | --- |
| Spruce | 38 | 13 |
| Spruce | 38 | 13 |
| Spruce | 38 | 15 |
| Spruce | 38 | 14 |
| Spruce | 37 | 15 |
| Spruce | 35 | 15 |
| Fir | 35 | 20 |
| Fir | 26 | 15 |

| Wood species | Resistance measured between the first and the second electrodes (kohms) | Humidity level measured after 288 hours (%) |
| --- | --- | --- |
| Fir | 25 | 15 |
| Fir | 25 | 15 |
| Fir | 23 | 15 |
| Fir | 23 | 17 |
| Fir | 22 | 18 |

| Wood species | Resistance measured between the first and the second electrodes (kohms) | Humidity level measured after 362 hours (%) |
| --- | --- | --- |
| Fir | 22 | 16 |
| Spruce | 21 | 17 |
| Fir | 21 | 16 |
| Fir | 20 | 20 |
| Fir | 10 | 21 |
| Fir | 5 | 25 |
| Fir | 5 | 31 |
| Fir | 5 | 33 |
| Fir | 5 | 34 |
| Fir | 5 | 39 |
| Fir | 5 | 35 |
| Fir | 5 | 49 |
| Fir | 5 | 41 |
| Fir | 5 | 43 |

The tests where performed by drying several wood pieces with a fan. The wood pieces were put outdoors and covered with a plastic so that rain water did not affect the results. Of course, the ambient humidity level could not be controlled and neither was the temperature, which ranged between 25 to 5 degrees Celsius. The humidity level was measured by means of a hygrometer made by the company DELMHORST.

As can be appreciated, these tests tend to show that certain ranges of measured resistance yield acceptable drying levels (below 19%) after a predetermined drying time. For example, measured values of 120 to 42 kohms give a drying time of 222 hours, measured values of 38 to 23 kohms give a drying time of 288 hours, while measured values under 22 kohms may yield drying times of longer than 288 hours.

Accordingly, an empirical relationship can be established between the measured current signals and the drying time of a piece of wood. This empirical relationship may be obtained as shown above by tabulating the measurement results of the current signals or the corresponding resistance values measured by the electrodes, and the humidity level measured after a predetermined drying time. This empirical relationship will of course vary depending on the particular drying conditions. For example, the empirical relationship will be modified if a more or less powerful dryer is used. Other factors affecting the empirical relationship depend on whether the drying occurs indoors or outdoors, or if the ambient humidity and temperature can be controlled or not. Once the empirical relationship is established, it can be entered in the program of the microcomputer or measuring circuit 35.

Similarly as for the determination of a drying time, an empirical relationship can be established for the homogeneity of the pieces of wood. The empirical results can be entered into the program of the microcomputer or measuring circuit 35. The homogeneity level data can be used similarly as above for sorting the pieces of wood in combination with the drying times. This homogeneity level may also be displayed by the microcomputer or can be transmitted to a sorting machine that can use the homogeneity data.

It should also be noted that the probe 9 may also be used without the conveyor 5 in certain circumstances. Accordingly, the probe 9 can be manually operated by a user who inserts the spiked ends of the probe 9 into the piece of wood to take the measurements. It goes without saying that such a technique is very time consuming if several pieces of wood are to be inspected. However, the use of the probe 9 without the conveyor 5 can be useful, for example, when making tests on a limited number of wood pieces. The apparatus would then consist of only the probe 9 and the measuring circuit 35, both of which being described above.

Also, instead of having all the electrodes in an aligned configuration, other arrangements of electrodes may possibly be suitable, as long as the current signals flowing from the second electrode to the first and third electrodes do not interfere with each other. For example, a triangular electrode configuration may be used.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. An apparatus for determining a drying time of a piece of wood, comprising:
    a conveyor adapted to transport the piece of wood along a travelling path;
    a probe mounted aside the travelling path, the probe having first and second electrodes extending next to one another and having spiked ends directed toward the travelling path for insertion into the piece of wood when the piece of wood transported by the conveyor passes by the probe, the second electrode having an input for receiving electric power, the first electrode having an output for transmission of a current signal having passed through the piece of wood from the second electrode to the first electrode;
    driving means for selectively driving the probe toward and away from the piece of wood between a measuring position where the spiked ends of the electrodes are stuck in the piece of wood and a retracted position where the spiked ends of the electrodes are withdrawn from the piece of wood;
    a control means connected to the driving means, for controlling operation thereof; and
    a measuring means coupled to the outputs of the electrodes, for measuring the current signal, and determining the drying time of the piece of wood based on the current signal.

2. The apparatus according to claim 1, wherein the probe has a third electrode extending next to the first and second electrodes, the third electrode having a substantially identical shape to the first electrode and an output for transmission of a current signal having passed through the piece of wood from the second electrode to the third electrode.

3. The apparatus according to claim 2, wherein the measuring means determine a homogeneity level of the piece of wood based on a difference between the current signals.

4. The apparatus according to claim 3, wherein the electrodes are aligned with and equally spaced apart from one another.

5. The apparatus according to claim 4, wherein the probe comprises at least one set of first, second and third additional electrodes projecting on sides of and being connected with the first, second and third electrodes respectively, the additional electrodes having substantially identical shapes to the electrodes connected therewith.

6. The apparatus according to claim 1, further comprising a probe moving means mounted on a side of the conveyor and supporting the driving means, for moving the probe upstream along the conveyor towards a subsequent piece of wood travelling on the travelling path once the current signal passing through the piece of wood has been measured by the measuring means.

7. The apparatus according to claim 6, wherein the probe moving means comprises:
    a guide frame mounted on the side of the conveyor, the guide frame having a slide arrangement slidably receiving and guiding the driving means along the conveyor;
    a chain assembly having a chain running around two spaced apart sprocket wheels mounted on the side of the conveyor at a given distance from the guide frame, the chain assembly being driven by the conveyor; and
    a rod extending between the guide frame and the chain assembly, the rod having an end pivotally connected to a link of the chain and an opposite end pivotally connected to the driving means.

8. The apparatus according to claim 7, wherein the driving means comprises:
    a base slidably mounted in the slide arrangement of the guide frame, the opposite end of the rod being attached to the base, the base having a slide arrangement extending substantially crosswise to the slide arrangement of the guide frame;
    a bracket extending over the conveyor and supporting the probe, the bracket being slidably mounted in the slide arrangement of the base for sliding toward and away the conveyor; and
    an actuator mounted onto the base and having an end connected to the bracket, the actuator being responsive to the control means.

9. The apparatus according to claim 8, further comprising an additional probe mounted aside the travelling path, both probes being identical and facing each other in a closable jaw arrangement biting the piece of wood by action of the driving means.

10. The apparatus according to claim 9, further comprising an additional jaw arrangement including facing probes as in the other jaw arrangement, both jaw arrangements operating identically and in unison, the additional jaw arrangements being spaced from each other along the conveyor so that the piece of wood and a successive piece of wood are processed simultaneously.

11. The apparatus according to claim 1, further comprising a detector mounted in front of the probe and connected to the control means, the detector generating a detection signal when the piece of wood approaches the probe.

12. The apparatus according to claim 11, wherein the detector comprises a photocell directed across the travelling path upstream of the probe.

13. The apparatus according to claim 1, wherein the control means and the measuring means are combined together into a microprocessor.

14. A method for determining a drying time of a piece of wood, using a probe having first and second electrodes extending next to one another and having spiked ends in a same direction, comprising the steps of:
    transporting the piece of wood along a travelling path;
    driving the probe against the piece of wood into a measuring position where the spiked ends of the electrodes are stuck in the piece of wood;
    applying electric power on the second electrode while the spiked ends of the electrodes are in the measuring position;
    measuring a current signal passing through the piece of wood from the second electrode to the first electrode;

removing the probe from the piece of wood into a retracted position where the spiked ends of the electrodes are withdrawn from the piece of wood when the current signal has been measured; and determining the drying time of the piece of wood based on the current signal.

15. The method according to claim 14, wherein the probe has a third electrode extending next to the first and second electrodes, the third electrode having a spiked end extending in the same direction as the other spiked ends, and wherein the method further comprises the steps of:

measuring a current signal passing through the piece of wood from the second electrode to the third electrode after the step of applying electric power on the second electrode; and determining a homogeneity level of the piece of wood based on a difference between the current signals.

16. An apparatus for determining a drying time of a piece of wood, comprising:

a probe having first and second electrodes extending next to one another and having spiked ends directed in a same direction for insertion into the piece of wood, the second electrode having an input for receiving electric power, the first electrode having an output for transmission of a current signal having passed through the piece of wood from the second electrode to the first electrode; and a measuring means coupled to the output of the first electrode, for measuring the current signal, and determining the drying time of the piece of wood based on the current signal.

17. The apparatus according to claim 16, wherein the probe has a third electrode extending next to the first and second electrodes, the third electrode having a substantially identical shape to the first electrode and an output for transmission of a current signal having passed through the piece of wood from the second electrode to the third electrode.

18. The apparatus according to claim 17, wherein the measuring means determine a homogeneity level of the piece of wood based on a difference between the current signals.

19. The apparatus according to claim 17, wherein the electrodes are aligned with and equally spaced apart from one another.

20. The apparatus according to claim 19, wherein the probe comprises at least one set of first, second and third additional electrodes projecting on sides of and being connected with the first, second and third electrodes respectively, the additional electrodes having substantially identical shapes to the electrodes connected therewith.

21. A method for determining a drying time of a piece of wood, using a probe having first and second electrodes extending next to one another and having spiked ends in a same direction, comprising the steps of:

driving the probe against the piece of wood into a measuring position where the spiked ends of the electrodes are stuck in the piece of wood;

applying electric power on the second electrode while the spiked ends of the electrodes are in the measuring position;

measuring a current signal passing through the piece of wood from the second electrode to the first electrode;

removing the probe from the piece of wood when the current signal has been measured; and determining the drying time of the piece of wood based on the current signal.

22. The method according to claim 21, wherein the probe has a third electrode extending next to the first and second electrodes, the third electrode having a spiked end extending in the same direction as the other spiked ends, and wherein the method further comprises the steps of:

measuring a current signal passing through the piece of wood from the second electrode to the third electrode after the step of applying electric power on the second electrode; and determining a homogeneity level of the piece of wood based on a difference between the current signals.

* * * * *